United States Patent [19]

Jäger et al.

[11] Patent Number: 4,578,396
[45] Date of Patent: Mar. 25, 1986

[54] FUNGICIDAL HYDROXYALKINYL-AZOLYL DERIVATIVES

[75] Inventors: Gerhard Jäger, Leverkusen; Klaus Böckmann, Cologne; Karl H. Büchel, Burscheid; Wilhelm Brandes, Leichlingen; Paul-Ernst Frohberger; Hans Scheinpflug, both of Leverkusen, all of Fed. Rep. of Germany

[73] Assignee: Bayer Aktiengesellschaft, Leverkusen, Fed. Rep. of Germany

[21] Appl. No.: 498,606

[22] Filed: May 27, 1983

[30] Foreign Application Priority Data

Jun. 12, 1982 [DE] Fed. Rep. of Germany ....... 3222191

[51] Int. Cl.$^4$ ................ A01N 43/50; A01N 43/653; C07D 233/60; C07D 249/08
[52] U.S. Cl. .................... 514/383; 514/184; 514/399; 548/101; 548/262; 548/341; 549/555; 568/645; 568/812; 568/838; 568/843; 568/849
[58] Field of Search ............... 548/262, 101, 341; 424/245, 269, 273 R; 514/184, 383, 399

[56] References Cited

U.S. PATENT DOCUMENTS 4,413,003 11/1983 Miller et al. ............... 548/341
4,414,210 11/1983 Miller et al. ............... 548/262

FOREIGN PATENT DOCUMENTS 0025516 3/1981 European Pat. Off. ........... 548/262
0033501 8/1981 European Pat. Off. ........... 548/341
0052424 5/1982 European Pat. Off. ........... 548/262
0071009 2/1983 European Pat. Off. ........... 548/262
3021551 12/1981 Fed. Rep. of Germany ...... 548/341

Primary Examiner—Alton D. Rollins
Attorney, Agent, or Firm—Sprung Horn Kramer & Woods

[57] ABSTRACT

Hydroxyalkinyl-azolyl derivatives of the formula

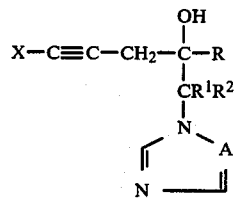

in which
A is a nitrogen atom or the CH group,
R is optionally substituted alkyl, cycloalkyl or phenyl,
$R^1$ is hydrogen, alkyl, alkenyl, alkinyl, or optionally substituted benzyl,
$R^2$ is hydrogen or methyl, and
X is hydrogen, bromine or iodine, or addition products thereof with acids or metal salts exhibit fungicidal activity. Some intermediates therefor are also new.

7 Claims, No Drawings

FUNGICIDAL HYDROXYALKINYL-AZOLYL DERIVATIVES

The present invention relates to new hydroxyalkinylazolyl derivatives, several processes for their preparation and their use as fungicides.

It has already been disclosed that certain hydroxyalkyl-triazoles, such as, for example, 2-(4-biphenylyl)-1-(2,4-dichlorophenyl)-3-(1,2,4-triazol-1-yl)-propan-2-ol or 2-(4-biphenylyl)-1-(4-chlorophenyl)-3-(1,2,4-triazol-1-yl)-propan-2-ol, possess fungicidal properties (see U.S. Application Ser. No. 144,102 filed Apr. 28, 1980, now abandoned. However, the activity of these compounds is not always completely satisfactory, particularly when low amounts and concentrations are used.

New hydroxyalkinyl-azolyl derivatives of the general formula $$X-C\equiv C-CH_2-\underset{\underset{\underset{N\diagup\diagdown A}{|}}{\overset{|}{CR^1R^2}}}{\overset{OH}{\overset{|}{C}}}-R \qquad (I)$$

in which
A represents a nitrogen atom or the CH group,
R represents optionally substituted alkyl, optionally substituted cycloalkyl or optionally substituted phenyl,
$R^1$ represents hydrogen, alkyl, alkenyl, alkinyl, or optionally substituted benzyl,
$R^2$ represents hydrogen or methyl and
X represents hydrogen, bromine or iodine, and their acid addition salts and metal salt complexes have been found.

Furthermore, it has been found that the hydroxyalkinyl-azolyl derivatives of the formula (I) are obtained when (a) azolyl-ketones of the formula $$R-CO-CR^1R^2-N\diagup\diagdown \qquad (II)$$

in which
A, R, $R^1$ and $R^2$ have the meaning given above, are reacted with propargyl halides of the formula $$HC\equiv C-CH_2-Hal \qquad (III)$$

in which
Hal represents halogen, in particular chlorine or bromine,
in the presence of activated aluminum and in the presence of a diluent, or (b) hydroxyalkinyl halides of the formula $$H-C\equiv C-CH_2-\underset{\underset{Hal'}{|}}{\overset{\overset{OH}{|}}{C}}\diagup\overset{R}{\diagdown}CR^1R^2 \qquad (IV)$$

in which
R, $R^1$ and $R^2$ have the meaning given above, and
Hal' represents halogen, in particular chlorine or bromine,
are reacted with azoles of the formula $$H-N\diagup\diagdown \qquad (V)$$

in which
A has the meaning given above, in the presence of a base and in the presence of a diluent,
or
(c) oxiranes of the formula $$H-C\equiv C-CH_2-\underset{O\diagdown\diagup CR^1R^2}{C}-R \qquad (VI)$$

in which
R, $R^1$ and $R^2$ have the meaning given above,
are reacted with azoles of the formula $$H-N\diagup\diagdown \qquad (V)$$

in which
A has the meaning given above,
in the presence of a diluent and, if appropriate, in the presence of a base, or (d) if appropriate, the hydroxyalkinyl-azolyl derivatives obtained by processes (a), (b) or (c), of the formula $$H-C\equiv C-CH_2-\underset{\underset{\underset{N\diagup\diagdown A}{|}}{\overset{|}{CR^1R^2}}}{\overset{OH}{\overset{|}{C}}}-R \qquad (Ia)$$

in which
A, R, $R^1$ and $R^2$ have the meaning given above, are reacted with an alkali metal hypohalite in a manner which is in itself known.

The resulting compounds of the formula (I) can, if desired, be subjected to an addition reaction with an acid or a metal salt.

Finally, it has been found that the new hydroxyalkinyl-azolyl derivatives of the formula (I) and their acid addition salts and metal salt complexes possess powerful fungicidal properties. In this respect, the compounds according to the invention surprisingly exhibit better fungicidal activity than the hydroxyalkyl-triazoles, such as, for example, 2-(4-biphenylyl)-1-(2,4-dichlorophenyl)-3-(1,2,4-triazol-1-yl)-propan-2-ol or 2-(4-biphenylyl)-1-(4-chlorophenyl)-3-(1,2,4-triazol-1-yl)-propan-2-ol, which are known from the prior art and are chemically similar compounds. The active compounds according to the invention thus represent an enrichment of the art.

Furthermore, the new hydroxyalkinyl-azolyl derivatives are interesting intermediate products. Thus, for example, the compounds of the general formula (I) can be converted in a conventional manner at the hydroxyl group to give the corresponding ethers. Furthermore, acyl or carbamoyl derivatives of the compounds of the general formula (I) can be obtained by reaction with, for example, acyl halides, isocyanates or carbamoyl chlorides in a manner which is known in principle.

Formula (I) gives a general definition of the hydroxyalkinyl-azolyl derivatives according to the invention. In this formula, R preferably represents straight-chain or branched alkyl having 1 to 4 carbon atoms, or cycloalkyl which has 3 to 7 carbon atoms and is optionally monosubstituted to trisubstituted by identical or different alkyl radicals having 1 to 4 carbon atoms, or preferably represents adamantyl, or phenyl which is optionally monosubstituted to trisubstituted by identical or different substituents, the following being preferably mentioned as substituents: halogen, alkyl having 1 to 4 carbon atoms, halogenoalkyl having 1 to 2 carbon atoms and 1 to 5 identical or different halogen atoms, such as, preferably, fluorine atoms and chlorine atoms, and optionally halogen-substituted phenyl; or preferably represents the groupings

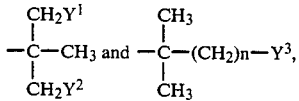

wherein $Y^1$ represents hydrogen or halogen, $Y^2$ represents halogen, and $Y^3$ represent alkyl, alkoxy and alkylthio, each having 1 to 4 carbon atoms, halogenoalkoxy and halogenoalkylthio, each having 1 to 2 carbon atoms and 1 to 5 identical or different halogen atoms, such as fluorine atoms and chlorine atoms, alkenyl having 2 to 6 carbon atoms, alkoxycarbonyl having 1 to 4 carbon atoms in the alkyl part, cyano, and phenyl which is optionally monosubstituted to trisubstituted by identical or different substituents, phenoxy, phenylthio, phenylalkoxy having 1 to 4 carbon atoms in the alkyl part and phenylalkylthio having 1 to 4 carbon atoms in the alkyl part, the following being preferably mentioned as phenyl substituents in each case: halogen, alkyl having 1 to 4 carbon atoms; alkoxy and alkylthio, each having 1 to 2 carbon atoms; halogenoalkyl, halogenoalkoxy and halogenoalkylthio, each having 1 to 2 carbon atoms and 1 to 5 identical or different halogen atoms, such as, in particular, fluorine atoms and chlorine atoms, cyclohexyl, dialkylamino having 1 to 4 carbon atoms in each alkyl part, nitro, cyano, and alkoxycarbonyl having 1 to 4 carbon atoms in the alkyl part; and optionally halogen-substituted phenyl; n represents the numbers 0, 1 or 2;

$R^1$ preferably represents hydrogen, straight-chain or branched alkyl having 1 to 4 carbon atoms, alkenyl and alkinyl, each having 2 to 4 carbon atoms, and benzyl which is optionally monosubstituted to trisubstituted by identical or different substituents, the phenyl substituents already mentioned as being preferred in the case of $Y^3$ being preferred phenyl substituents; and A, $R^2$ and X preferably have the meanings given in the definition of the invention.

Particularly preferred compounds of the formula (I) are those in which

R represents tert.-butyl, isopropyl or methyl, or cyclopropyl, cyclopentyl or cyclohexyl, each of which is optionally monosubstituted or disubstituted by identical or different substituents from amongst methyl, ethyl, isopropyl or tert.-butyl, or represents adamantyl, or phenyl which is optionally monosubstituted or disubstituted by identical or different substituents, the following being mentioned as substituents: fluorine, chlorine, methyl, trifluoromethyl, and optionally chlorine-substituted phenyl, or represents the groupings

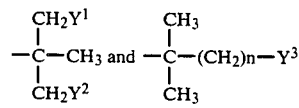

wherein $Y^1$ represents hydrogen, fluorine, chlorine or bromine, $Y^2$ represents fluorine, chlorine or bromine, $Y^3$ represents methyl, ethyl, n-propyl, isopropyl, tert.-butyl, methoxy, ethoxy, methylthio, ethylthio, trifluoromethoxy, trifluoromethylthio, vinyl, methoxycarbonyl, ethoxycarbonyl or cyano, and represents phenoxy, phenylthio, phenylmethoxy, phenylmethylthio and phenyl which is optionally monosubstituted or disubstituted by identical or different substituents, the following being mentioned as phenyl substituents in each case: fluorine, chlorine, bromine, methyl, ethyl, isopropyl, tert.-butyl, methoxy, methylthio, ethoxy, trifluoromethyl, trifluoromethoxy, trifluoromethylthio, nitro, dimethylamino, methoxycarbonyl and optionally chlorine-substituted phenyl, and n represents the numbers 0, 1 or 2, $R^1$ represents hydrogen, methyl, vinyl, allyl, propargyl, and benzyl which is optionally monosubstituted or disubstituted by identical or different substituents, the phenyl substituents already mentioned as preferred in the case of $Y^3$ being preferred phenyl substituents, and A, $R^2$ and X have the meanings given in the definition of the invention.

Preferred compounds according to the invention are also addition products of acids and those hydroxyalkinyl-azolyl derivatives of the formula (I), in which the substituents A, R, $R^1$, $R^2$ and X have the meanings which have already been mentioned as being preferred for these substituents.

Acids which can be used to form addition products preferably include hydrohalic acids, such as, for example, hydrochloric acid and hydrobromic acid, in particular hydrochloric acid, and also phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, as well as sulphonic acids, such as, for example, p-toluenesulphonic acid and naphthalene-1,5-disulphonic acid.

Further preferred compounds according to the invention are addition products of salts of metals of main groups II to IV and of sub-groups I and II and IV to VIII and those hydroxyalkinyl-azolyl derivatives of the formula (I) in which substituents A, R, $R^1$, $R^2$ and X have the meanings which have already been mentioned as being preferred for these substituents.

In this context, salts of copper, zinc, manganese, magnesium, tin, iron and nickel are particularly preferred. Suitable anions of these salts are those which are derived from those acids which lead to physiologically tolerated addition products. In this connection, particularly preferred acids of this type are hydrohalic acids, such as, for example, hydrochloric acid and hydrobromic acid, and also phosphoric acid, nitric acid and sulphuric acid.

If, for example, 5-(2,4-dichlorophenoxy)-3,3-dimethyl-1-(1,2,4-triazol-1-yl)-pentan-2-one and propargyl bromide are used as starting materials in the presence of aluminum and catalytic amounts of mercury(II) chloride, the course of process (a) according to the invention can be represented by the following equation:

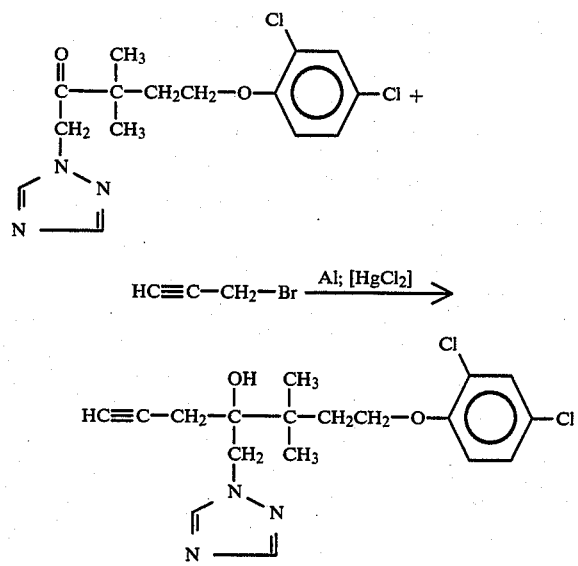

If, for example, 5-chloro-4-(2,4-dichlorophenyl)pent-1-in-4-ol and imidazole are used as starting materials, the course of process (b) according to the invention can be represented by the following equation:

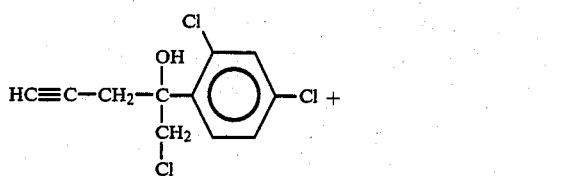

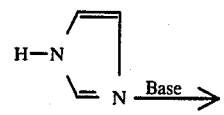

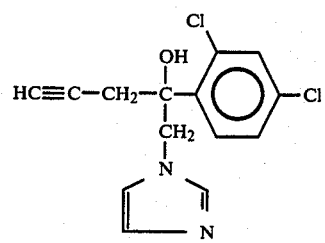

If, for example, 2-(3,4-dichlorophenyl)-2-propargyl-oxirane and 1,2,4-triazole are used as starting materials, the course of process (c) according to the invention can be represented by the following equation:

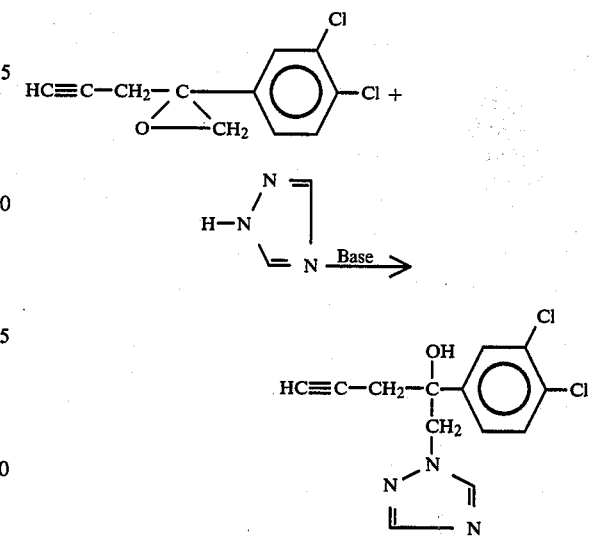

If, for example, 4-tert.-butyl-6-(4-chlorophenyl)-5-(1,2,4-triazol-1-yl)-hex-1-in-4-ol and potassium hypobromite are used as starting materials, the course of the reaction in process (d) according to the invention can be represented by the following equation:

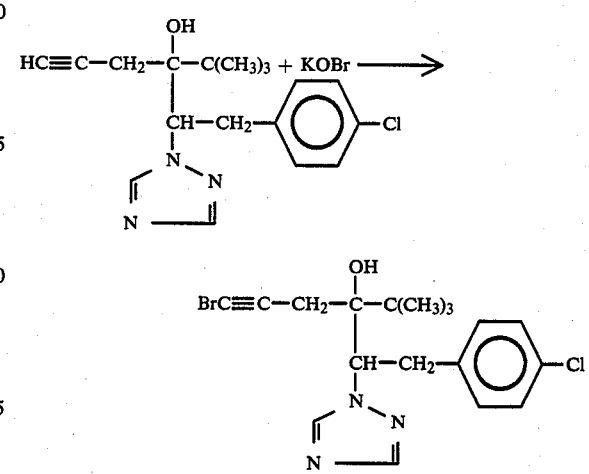

Formula (II) gives a general definition of the azolyl-ketones to be used as starting materials in carrying out process (a) according to the invention. In this formula, A, R, $R^1$ and $R^2$ preferably have those meanings which have already been mentioned in connection with the description of the substances according to the invention, of the formula (I), as being preferred for these substituents.

The azolyl-ketones of the formula (II) are substantially known (see, for example U.S. Application Ser. No. 291,700 filed Aug. 10, 1981, now pending, DE-OS [German Published Specification] No. 2,610,022, DE-OS [German Published Specification] No. 2,638,470, U.S. Application Ser. No. 321,291 filed Nov. 13, 1981, now abandoned, U.S. Applications Ser. No. 328,871 filed Dec. 8, 1981, now abandoned, Ser. No. 438,086 filed Nov. 1, 1982, now pending and Ser. No. 438,087 filed Nov. 1, 1982, now U.S. Pat. No. 4,492,795; or they can be obtained in a generally customary manner.

The propargyl halides of the formula (III) which are furthermore to be used as starting materials for process (a) according to the invention are generally known compounds of organic chemistry.

Formula (IV) gives a general definition of the hydroxyalkinyl halides to be used as starting materials in carrying out process (b) according to the invention. In this formula, R, $R^1$ and $R^2$ preferably have the meanings which have already been mentioned in connection with the description of the substances according to the invention, of the formula (I), as being preferred for these substituents.

The hydroxyalkinyl halides of the formula (IV) are not yet known; however, they can be obtained in a simple manner by reacting halogenoketones of the formula

R—CO—CR$^1$R$^2$—Hal'      (VII)

in which

Hal, R, $R^1$ and $R^2$ have the meaning given above, with propargyl halides of the formula (III), according to process (a).

Halogenoketones of the formula (VII) are known and can be obtained in a generally known manner.

Formula (VI) gives a general definition of the oxiranes to be used as starting materials in carrying out process (c) according to the invention. In this formula, R, $R^1$ and $R^2$ preferably have the meanings which have already been mentioned in connection with the description of the substances according to the invention, of the formula (I) as being preferred for these substituents.

The oxiranes of the formula (VI) are not yet known; however, they can be obtained in a simple manner by reacting hydroxyalkinyl halides of the formula (IV) with a base, such as, for example, potassium carbonate, in a two-phase system, such as, for example, methylene chloride/water, in the presence a phase-transfer catalyst, such as, for example, triethylbenzylammonium chloride, at temperatures between 20° and 50° C.

Formula (I) gives a general definition of the azoles furthermore to be used as starting materials for processes (b) and (c) according to the invention. In this formula, A preferably has the meanings which have already been mentioned in the definition of the invention.

The azoles of the formula (V) are generally known compounds of organic chemistry.

The hydroxyalkinyl-azolyl derivatives of the formula (Ia) to be used as starting materials for process (d) according to the invention are compounds according to the invention.

Suitable diluents for process (a) according to the invention are organic, aprotic solvents, such as, for example, diethyl ether or tetrahydrofuran.

The reaction according to process (a) is carried out in the presence of activated aluminum. This is achieved by adding catalytic amounts of mercury(II) chloride and iodine.

In carrying out process (a) according to the invention, the reaction temperatures can be varied within a relatively wide range. In general, the reaction is carried out at temperatures between −80° and 100° C., preferably between −70° and 60° C.

In carrying out process (a) according to the invention, 1 to 2 mols of propargyl halide of the formula (III) and 1 to 1.5 mols of aluminum and catalytic amounts of mercury(II) chloride and iodine are preferably employed per mol of azolyl-ketone of the formula (II). The end products are isolated in a generally customary manner.

Preferred diluents for process (b) according to the invention are polar organic solvents. These preferably include alcohols, such as methanol, ethanol, propanol, isopropanol, butanol or isobutanol; nitriles, such as acetonitrile or propionitrile; amides, such as dimethylformamide, formamide or dimethylacetamide; and sulphoxides, such as dimethylsulphoxide or sulpholane.

Suitable bases for process (b) according to the invention are all inorganic and organic bases which can customarily be used. These preferably include alkali metal carbonates, such as potassium carbonate or sodium carbonate; alkali metal alcoholates, such as sodium methylate and ethylate or potassium methylate and ethylate; alkali metal hydrides, such as sodium hydride; tertiary amines, such as triethylamine or benzyldimethylamine; and also azoles of the formula (V) or their alkali metal salts.

In carrying out process (b) according to the invention, the reaction temperatures can be varied within a relatively wide range. In general, the reaction is carried out at temperatures between 20° and 150° C., preferably between 40° and 120° C.

In carrying out process (b) according to the invention, 1 to 2 mols of azole of the formula (V) and 1 to 4 mols of base are preferably employed per mol of hydroxyalkinyl halide of the formula (IV). The end products are isolated in a generally customary manner.

Suitable diluents for process (c) according to the invention are organic solvents which are inert under the reaction conditions. These preferably include alcohols, such as methanol, ethanol, propanol, isopropanol, butanol or isobutanol; nitriles, such as acetonitrile; esters, such as ethyl acetate; ethers, such as dioxane; amides, such as dimethylformamide; and aromatic hydrocarbons, such as benzene and toluene.

Suitable bases for process (c) according to the invention are all inorganic and organic bases which can customarily be used. These preferably include the bases already mentioned in the case of process (b) as being preferred.

In carrying out process (c) according to the invention, the reaction temperatures can be varied within a relatively wide range. In general, the reaction is carried out at temperatures between 20° and 150° C., preferably between 40° and 120° C.

In carrying out process (c) according to the invention, 1 to 2 mols of azole of the formula (V) and, if appropriate, catalytic to molar amounts of a base are preferably employed per mol of oxirane of the formula (VI). The end products are isolated in a generally customary manner.

Suitable diluents for process (d) according to the invention are water and organic solvents which are inert to alkali metal hypohalites. These preferably include alcohols, such as methanol or ethanol; ethers, such as diethyl ether, dioxane or tetrahydrofuran; and also two-phase mixtures, such as, for example, ether/water.

In carrying out process (d) according to the invention, the reaction temperatures can be varied within a relatively wide range. In general, the reaction is carried out at temperatures between 0° and 60° C., preferably between 0° and 40° C.

In carrying out process (d) according to the invention, 1 to 1.5 mols of hypohalite are preferably employed per mol of the compound of the formula (Ia), the alkali metal hypohalite being produced in situ from the appropriate halogen and the alkali metal hydroxide, in particular sodium hydroxide and potassium hydroxide. The end products are isolated in a generally customary manner.

Preferred acids for the preparation of acid addition salts of the compounds of the formula (I) are those which have already been mentioned in connection with the description of the acid addition salts according to the invention as being preferred acids.

The acid addition salts of the compounds of the formula (I) can be obtained in a simple manner according to customary salt formation methods, by dissolving a compound of the formula (I) in a suitable solvent and adding the acid, for example hydrochloric acid, and can be isolated in a known manner, for example by filtration, and if appropriate purified by washing with an inert organic solvent.

Preferred salts for the preparation of metal salt complexes of compounds of the formula (I) are salts of those anions and cations which have already been mentioned in connection with the description of the metal salt complexes according to the invention as being preferred.

The metal salt complexes of compounds of the formula (I) can be obtained in a simple manner according to customary processes, thus, for example, by dissolving the metal salt in an alcohol, for example ethanol, and adding the solution to the compound of the formula (I). Metal salt complexes can be isolated in a known manner, for example by filtration, and if appropriate purified by recrystallisation.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Venturia species, such as against the apple scab causative organism (*Venturia inaequalis*), Erysiphe species, such as against the powdery mildew of barley causative organism (*Erysiphe graminis*), further cereal diseases, such as *Cochliobolus sativus* and *Pyrenophora teres,* and rice diseases, such as *Pyricularia oryzae* and *Pellicularia sasakii.* The additional bactericidal action should be singled out.

The active compounds can be converted to the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkali naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinylacetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

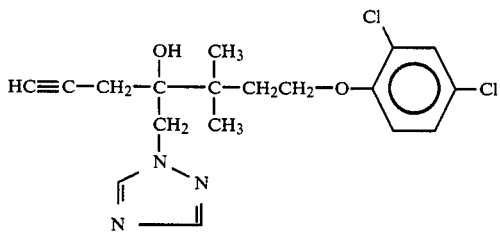

1.58 g (0.058 mol) of aluminum (in the form of flakes) are covered with a layer of 7.3 ml of tetrahydrofuran, and a catalytic amount (0.05 g) of mercury(II) chloride and an iodine crystal are added. After the mixture has stood for 12 hours at 20° C., 10.3 g (0.087 mol) of propargyl bromide in 11 ml of tetrahydrofuran are added dropwise at 60° C. The mixture is then cooled to −60° C., and a solution of 17.1 g (0.05 mol) of 5-(2,4-dichlorophenoxy)-3,3-dimethyl-1-(1,2,4-triazol-1-yl)pentan-2-one in 20 ml of tetrahydrofuran is added dropwise. The mixture is allowed to warm up to 0° C. and is kept for a further hour at this temperature, and 22 ml of a saturated, aqueous ammonium chloride solution are added. Thereafter, the mixture is filtered, the filtrate is evaporated down in vacuo and the residue is taken up in 200 ml of ethyl acetate. After the solution has been washed with three times 100 ml of water, the organic phase is dried over sodium sulphate and then evaporated down in vacuo. Residues of solvent are removed at 50° C. and 0.01 mbar. 14.3 g (74.8% of theory) of 7-(2,4-dichlorophenoxy)-5,5-dimethyl-4-(1,2,4-triazol-1-yl-methyl)-hept-1-in-4-ol are obtained as a brownish oil of refractive index $n_D^{20} = 1.5642$.

Preparation of the starting material

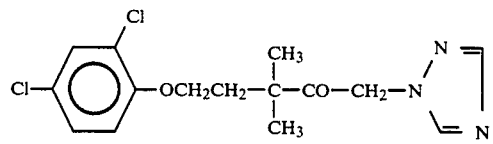

30.9 g (0.1 mol) of 1-chloro-5-(2,4-dichlorophenoxy)-3,3-dimethyl-pentan-2-one, dissolved in 80 ml of acetone, are added dropwise to a stirred mixture of 13.8 g (0.1 mol) of potassium carbonate and 13.8 g (0.2 mol) of 1,2,4-triazole in 200 ml of boiling acetone. The mixture is kept at the boil for a further 3 hours, cooled to 0° to 10° C. and filtered off from the salt, and the filtrate is evaporated down in vacuo. After the oily residue has been triturated with a little petroleum ether, 32.4 g (94.5% of theory) of 5-(2,4-dichlorophenoxy)-3,3-dimethyl-1-(1,2,4-triazol-1-yl)-pentan-2-one are obtained as colorless crystals of melting point 62° C.

Example 2

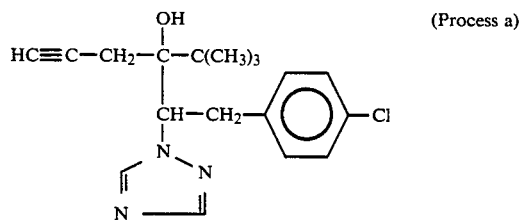

(Process a)

3.7 g of aluminum (in the form of flakes), a pinch of mercury(II) chloride and an iodine crystal are stirred with 20 ml of absolute tetrahydrofuran for 12 hours. 24 g (0.2 mol) of propargyl bromide, dissolved in 25 ml of tetrahydrofuran, are then added dropwise at 50° to 60° C. The mixture is stirred for a further 30 minutes at 60° C. and cooled to −60° C., and 29.2 g (0.1 mol) of 5-(4-chlorophenyl)-2,2-dimethyl-4-(1,2,4-triazol-1-yl)-pentan-3-one in 100 ml of tetrahydrofuran are slowly added dropwise. Thereafter, the reaction mixture is stirred for a further hour at 0° C. and for 2 hours at 20° C., 50 ml of saturated, aqueous ammonium chloride solution are added, while cooling, the mixture is filtered and the filtrate is evaporated down. The remaining crystalline residue is digested with water and recrystallized from 520 ml of cyclohexane. 24.6 g (74.2% of theory) of 4-tert.-butyl-6-(4-chlorophenyl)-5-(1,2,4-triazol-1-yl)-hex-1-in-4-ol of melting point 121° C. are obtained.

Preparation of the precursor

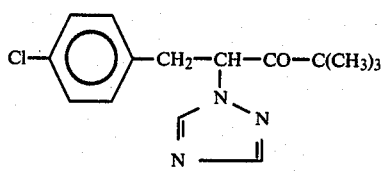

7.5 g (0.25 mol) of sodium hydride (80% strength suspension in oil) are slowly introduced, at 10° C., into a solution of 50.1 g (0.3 mol) of 2,2-dimethyl-4-(1,2,4-triazol-1-yl)-butan-3-one in 150 ml of absolute N,N-dimethylformamide, and the mixture is stirred at 20° C. until the evolution of gas has ended. A solution of 62 g (0.3 mol) of 4-chlorobenzyl bromide in 50 ml of N,N-dimethylformamide is then added dropwise, while stirring. After 5 hours, the reaction mixture is stirred into 900 ml of water, and the solid product which separates out is filtered off and recrystallized from 175 ml of ethanol. 55.6 g (76.3% of theory) of 5-(4-chlorophenyl)-2,2-dimethyl-4-(1,2,4-triazol-1-yl)-pentan-3-one are obtained in the form of colorless crystals of melting point 124° C.

Example 3

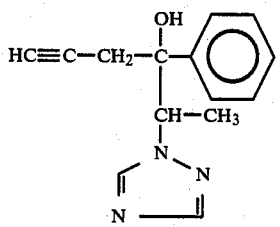 (Process a)

6.5 g (0.241 mol) of aluminum (in the form of flakes), a pinch of mercury(II) chloride and an iodine crystal are stirred for 12 hours together with 35 ml of tetrahydrofuran. 42 g (0.35 mol) of propargyl bromide in 50 ml of tetrahydrofuran are then added dropwise at 50° to 60° C. The mixture is stirred for a further 30 minutes at 60° C. and cooled to −60° C., and 34.2 g (0.17 mol) of 2-(1,2,4-triazol-1-yl)-propiophenone in 150 ml of tetrahydrofuran are slowly added dropwise at this temperature. After the addition is complete, the mixture is stirred for a further hour at 0° C. and for 2 hours at room temperature, 85 ml of saturated, aqueous ammonium chloride solution are added dropwise while cooling externally, the mixture is filtered and the filtrate is evaporated down in vacuo. The residue is extracted with three times 150 ml of ethyl acetate/toluene (1:1), and the combined organic phases are washed with water, dried over anhydrous sodium sulphate and evaporated down in vacuo. After the solid residue has been stirred with 40 ml of toluene, 18.7 g (45.6% of theory) of 4-phenyl-5-(1,2,4-triazol-1-yl)-hex-1-in-4-ol are obtained in the form of colorless crystals of melting point 123° C.

Preparation of the precursor

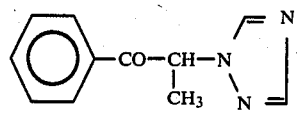

To a solution of 223 g (1 mol) of 2-bromopropiophenone in 300 ml of acetonitrile is added dropwise to a boiling mixture of 414 g (6 mols) of triazole and 1,200 ml of acetonitrile, and the mixture is heated at the boil for 8 hours. Thereafter, the mixture is evaporated down in vacuo, the residue is taken up in 750 ml of dichloromethane and 750 ml of water, and the organic phase is washed with several 500 ml portions of water and dried over anhydrous sodium sulphate. After the solvent has been distilled off, the remaining residue is distilled in vacuo. 111 g (55% of theory) of 2-(1,2,4-triazol-1-yl)-propiophenone of boiling point 133° C./0.15 mbar and of melting point 117° C. are obtained.

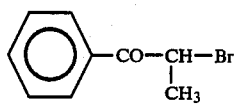

A solution of 82 g (0.51 mol) of bromine in 100 ml of dichloromethane is added dropwise to a solution of 72 g (0.5 mol) of propiophenone in 500 ml of dichloromethane, at 20° C. After 30 minutes, the solution is evaporated down. 2-Bromopropiophenone is obtained quantitatively, and is directly reacted further.

Example 4

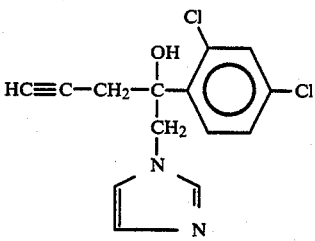 (Process b)

26.4 g (0.1 mol) of 5-chloro-4-(2,4-dichlorophenyl)-pent-1-in-4-ol, dissolved in 30 ml of n-propanol, are added dropwise to a boiling solution of 40.8 g (0.6 mol) of imidazole in 250 ml of n-propanol. After 48 hours, the solution is evaporated down in vacuo, the oily residue is taken up in 150 ml of ethyl acetate, and the organic phase is washed with three times 50 ml of water. By evaporating down the solution, 19 g (64.4% of theory) of 4-(2,4-dichlorophenyl)-5-imidazol-1-yl-pent-1-in-4-ol are obtained as colorless crystals of melting point 179°–180° C.

Preparation of the precursor

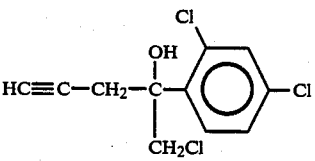

A pinch of mercury(II) chloride and an iodine crystal are added to 13 g (0.48 mol) of aluminum (in the form of flakes), the substances are covered with a layer of 60 ml of tetrahydrofuran and the mixture is stirred for 10 hours at 20° C. The mixture is then warmed to 60° C., and a solution of 84.5 g (0.71 mol) of propargyl bromide in 85 ml of tetrahydrofuran is added dropwise. The mixture is then cooled to −60° C., and a solution of 111.7 g (0.5 mol) of ω-chloro-2,4-dichloroacetophenone in 165 ml of tetrahydrofuran is added dropwise. The mixture is allowed to warm up to 0° C., and after 1 hour hydrolysis is effected with 170 ml of saturated, aqueous ammonium chloride solution. Thereafter, the mixture is filtered, the filtrate is evaporated down in vacuo and 500 ml of ethyl acetate are added to the residue. The organic phase is separated off, washed with three times 300 ml of water and dried over anhydrous sodium sulphate, and the solvent is distilled off under reduced pressure. 113.5 g (86.1% of theory) of 5-chloro-4-(2,4-dichlorophenyl)-pent-1-in-4-ol are obtained as colorless crystals of melting point 55°–57° C.

Example 5

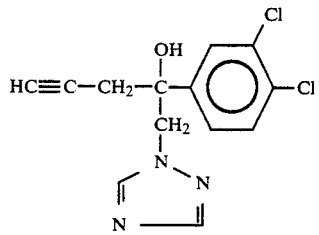
(Process c)

0.275 g (0.011 mol) of sodium is introduced into a boiling solution of 8.05 g (0.116 mol) of 1,2,4-triazole in 400 ml of n-butanol. 24 g (0.105 mol) of 2-(3,4-dichlorophenyl)-2-propargyl-oxirane, dissolved in 50 ml of n-butanol, are then added. The solution is heated at the boil for 12 hours, the solvent is distilled off in vacuo, the residue is taken up in 200 ml of trichloromethane, the solution is washed with twice 50 ml of water, and the organic phase is dried over anhydrous sodium sulphate and then filtered over 200 g of silica gel. 18.45 g (53.6% of theory) of 4-(3,4-dichlorophenyl)-5-(1,2,4-triazol-1-yl)-pent-1-in-4-ol are obtained as colorless crystals of melting point 114° C.

Preparation of the precursor

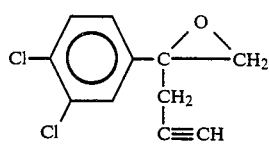

60.3 g (0.196 mol) of 5-bromo-4-(3,4-dichlorophenyl)-prop-1-in-4-ol are stirred together with 17 g of triethylbenzylammonium chloride and 460 g of potassium carbonate in a two-phase system comprising 1,800 ml of dichloromethane and 850 ml of water, for 8 hours at 20° to 25° C. 500 ml of tetrachloromethane are then added, and the organic phase is separated off and washed several times with water. After the organic phase has been evaporated down in vacuo, the oily residue is filtered over 200 g of silica gel (mobile phase: tetrachloromethane), and the filtrate is evaporated down under reduced pressure. 38 g (86% of theory) of 2-(3,4-dichlorophenyl)-2-propargyloxirane of refractive index $n_D^{20} = 1.5676$ are obtained.

Example 6

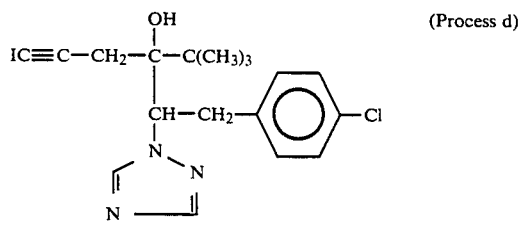
(Process d)

9.9 g (0.03 mol) of 4-tert.-butyl-6-(4-chlorophenyl)-5-(1,2,4-triazol-1-yl)-hex-1-in-4-ol are dissolved in 100 ml of methanol, and 9.2 g (0.036 mol) of iodine are introduced into the ice-cooled solution at the same time as 14.5 ml of 50% strength potassium hydroxide solution are being added dropwise. The mixture is stirred for a further 4 hours at room temperature, and the crystalline precipitate is filtered off under suction, washed with water and dried. 10.7 g (78% of theory) of 4-tert.-butyl-6-(4-chlorophenyl)-1-iodo-5-(1,2,4-triazol-1-yl)-hex-1-in-4-ol of melting point 155° C. are obtained.

The following compounds of the general formula

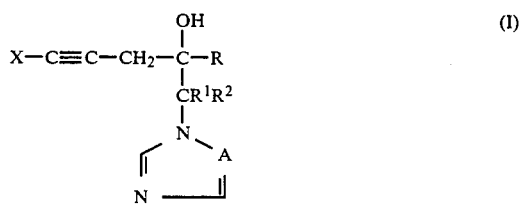
(I)

are obtained in an analogous manner and by processes (a) to (d) according to the invention:

| Example No. | R | R¹ | R² | X | A | Melting point (°C.) or refractive index ($n_D^{20}$) |
|---|---|---|---|---|---|---|
| 7 | —C(CH₃)₃ | H | H | H | N | 58–60 |
| 8 | —C(CH₃)₂—CH=CH₂ | H | H | H | N | 1.5220 |
| 9 | —C(CH₃)₂—CH₂Cl | H | H | H | N | 1.5293 |
| 10 | —C(CH₂Cl)₂CH₃ | H | H | H | N | 1.5431 |
| 11 | —C(CH₃)₂—CH₂F | H | H | H | N | viscous oil |

-continued

| Example No. | R | R$^1$ | R$^2$ | X | A | Melting point (°C.) or refractive index (n$_D^{20}$) |
|---|---|---|---|---|---|---|
| 12 | —C(CH$_3$)$_2$—O—⟨C$_6$H$_4$⟩—Cl | H | H | H | N | 96–97 |
| 13 | —C(CH$_2$F)$_2$CH$_3$ | H | H | H | N | viscous oil |
| 14 | —C(CH$_3$)$_2$—CH(CH$_3$)$_2$ | H | H | H | N | 1.5171 |
| 15 | —C(CH$_2$F)$_2$CH$_3$ | H | H | H | CH | 118–20 |
| 16 | —C(CH$_3$)$_2$—CH$_2$CH$_2$—O—⟨C$_6$H$_4$⟩—Cl | H | H | H | N | 1.5602 |
| 17 | —C(CH$_3$)$_2$—CH$_2$CH$_2$—O—⟨C$_6$H$_5$⟩ | H | H | H | CH | 69–70 |
| 18 | —C(CH$_3$)$_2$—CH$_2$CH$_2$—O—⟨C$_6$H$_3$⟩(Cl)(Cl) | H | H | H | CH | 133 |
| 19 | —C(CH$_3$)$_2$—CH$_2$CH$_2$—O—⟨C$_6$H$_4$⟩—Cl | H | H | H | CH | 85–87 |
| 20 | —C(CH$_3$)$_2$—CH$_2$—O—⟨C$_6$H$_4$⟩—Cl | H | H | H | N | resin |
| 21 | —C(CH$_3$)$_2$—CH$_2$F | H | H | H | CH | 92–93 |
| 22 | —C(CH$_3$)$_3$ | H | H | H | CH | 128 |
| 23 | —C(CH$_3$)$_2$—CH$_2$CH$_2$—O—⟨C$_6$H$_5$⟩ | H | H | H | N | resin |
| 24 | CH$_3$-cyclohexyl(H) | H | H | H | CH | 139–40 |
| 25 | Adamantyl | H | H | H | CH | 182 |
| 26 | —C(CH$_3$)$_2$—CH$_2$—C(CH$_3$)$_3$ | H | H | H | N | n$_D^{25}$: 1.4928 |
| 27 | Adamantyl | H | H | H | N | 116 |
| 28 | —C(CH$_3$)$_2$—CH$_2$—C(CH$_3$)$_3$ | H | H | H | CH | 143 |
| 29 | ⟨C$_6$H$_4$⟩—Cl | H | H | H | N | 142 |
| 30 | ⟨C$_6$H$_5$⟩ | H | H | H | N | 1.5745 |
| 31 | Cl—⟨C$_6$H$_3$⟩—Cl | H | H | H | N | 169–70 |
| 32 | ⟨C$_6$H$_4$⟩—Cl | H | H | H | CH | 120–21 |
| 33 | ⟨C$_6$H$_4$⟩—⟨C$_6$H$_5$⟩ | H | H | H | CH | 117–18 |

-continued
| Example No. | R | R¹ | R² | X | A | Melting point (°C.) or refractive index ($n_D^{20}$) |
|---|---|---|---|---|---|---|
| 34 |  | H | H | H | CH | 113 |
| 35 | 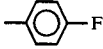 | H | H | H | CH | 106 |
| 36 | 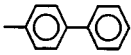 | H | H | H | N | resin |
| 37 | 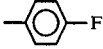 | H | H | H | N | 118 |
| 38 | 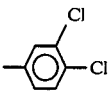 | H | H | H | CH | 116 |
| 39 | —C(CH₃)₃ | 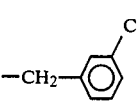 | H | H | H | N | 119–20 |
| 40 | —C(CH₃)₃ | 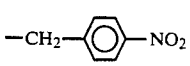 | H | H | N | 90–91 |
| 41 | —C(CH₃)₃ | 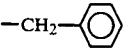 | H | H | N | 124 |
| 42 |  | CH₃ | H | H | CH | viscous oil |
| 43 | —C(CH₃)₂CH₂F | 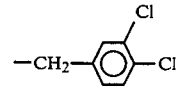 | H | H | N | 128 |
| 44 | —C(CH₃)₃ | 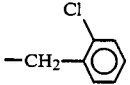 | H | H | N | 80–90 |
| 45 | —C(CH₃)₃ | 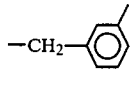 | H | H | N | 103–04 |
| 46 | —C(CH₃)₃ | 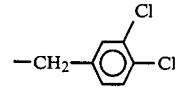 | H | H | N | 82 |
| 47 | —C(CH₃)₃ | 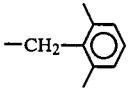 | H | H | N | 119 |
| 48 | —C(CH₃)₃ | 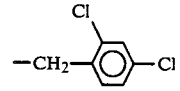 | H | H | N | 121 |
| 49 | —C(CH₃)₃ | 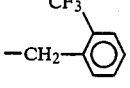 | H | H | N | 116 |

-continued

| Example No. | R | R¹ | R² | X | A | Melting point (°C.) or refractive index ($n_D^{20}$) |
|---|---|---|---|---|---|---|
| 50 | -C₆H₄-Cl | H | H | I | N | 108–09 |
| 51 | -C₆H₅ | H | H | I | N | resin |
| 52 | -C₆H₃(Cl)(Cl) (2,4-di-Cl) | H | H | I | CH | 171–72 |
| 53 | -C₆H₃(Cl)(Cl) (2,4-di-Cl) | H | H | I | N | 156 |
| 54 | -C₆H₄-C₆H₅ | H | H | I | CH | 114 |
| 55 | -C₆H₄-C₆H₅ | H | H | I | N | 104–05 |
| 56 | -C₆H₅ | H | H | I | CH | 93 |
| 57 | -C₆H₄-F | H | H | I | CH | 146–48 |
| 58 | -C₆H₄-F | H | H | I | N | viscous oil |
| 59 | -C(CH₃)₃ | H | H | I | N | 126 |
| 60 | -C(CH₃)₂-CH₂Cl | H | H | I | N | 100–02 |
| 61 | -C(CH₃)₂O-C₆H₄-Cl | H | H | I | N | 118–19 |
| 62 | -C(CH₃)₃ | H | H | I | CH | 140 |
| 63 | -C(CH₃)₂-CH₂O-C₆H₄-Cl | H | H | I | N | resin |
| 64 | -C(CH₃)₃ | -CH₂-C₆H₃(Cl)(Cl) (2,6-di-Cl) | H | I | N | 125 |
| 65 | -C(CH₃)₃ | -CH₂-C₆H₃(Cl)(Cl) (2,4-di-Cl) | H | I | N | 158 |
| 66 | -C(CH₃)₃ | -CH₂-C₆H₄-CF₃ (2-CF₃) | H | I | N | 135 |
| 67 | -C(CH₃)₃ | -CH₂-C₆H₄-CF₃ (3-CF₃) | H | I | N | 54 |
| 68 | -C(CH₃)₃ | -CH₂-C₆H₄-NO₂ | H | I | N | 181 |

-continued

| Example No. | R | R¹ | R² | X | A | Melting point (°C.) or refractive index ($n_D^{20}$) |
|---|---|---|---|---|---|---|
| 69 | −C(CH₃)₂−CH₂F | −CH₂−(3,4-Cl₂-C₆H₃) | H | I | N | 151–56 |
| 70 | −C(CH₃)₃ | −CH₂−(2-Cl-C₆H₄) | H | I | N | 109 |
| 71 | −C(CH₃)₃ | −CH₂−(3-Cl-C₆H₄) | H | I | N | 107 |
| 72 | −C(CH₃)₃ | −CH₂−C₆H₅ | H | I | N | 144 |
| 73 | −C₆H₅ | −CH₃ | H | I | CH | 159 |
| 74 | −C₆H₅ | −CH₃ | H | I | N | 112 |
| 75 | −C(CH₃)₃ | −CH₂−(3,4-Cl₂-C₆H₃) | H | I | N | 124 |
| 76 | −(4-Br-C₆H₄) | H | H | H | CH | 136 |
| 77 | cyclohexyl-CH(CH₃)− | H | H | H | N | 96–97 |
| 78 | −C(CH₃)₂−i-C₃H₇ | H | H | H | CH | 128–31 |
| 79 | −C(CH₃)₂−CH₂CH₂−O−(C₆H₄)−C₆H₅ | H | H | H | CH | 159–60 |
| 80 | −C(CH₃)₂−(4-Cl-C₆H₄) | H | H | H | CH | 136–37 |
| 81 | −C(CH₃)₂−CH₂CH₂−O−(2-Cl-C₆H₄) | H | H | H | CH | 104–05 |
| 82 | −C(CH₃)₂−CH₂−(4-CH₃-C₆H₄) | H | H | H | N | 117–18 |
| 83 | −C(CH₃)₂−CH₂−S−(4-Cl-C₆H₄) | H | H | H | N | 1.5852 |
| 84 | −C(CH₃)₂−CH₂−(4-Cl-C₆H₄) | H | H | H | N | 110–11 |
| 85 | −C(CH₃)₂−O−(C₆H₄)−C₆H₅ | H | H | H | CH | 118–20 |
| 86 | −C(CH₃)₂−O−(C₆H₄)−C₆H₅ | H | H | H | N | viscous oil |

-continued
| Example No. | R | R¹ | R² | X | A | Melting point (°C.) or refractive index ($n_D^{20}$) |
|---|---|---|---|---|---|---|
| 87 |  | 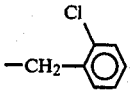 | H | H | N | 120–25 |
| 88 |  | 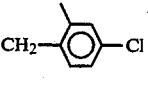 | H | H | N | 94–99 |
| 89 |  | 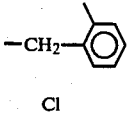 | H | I | N | 128–30 |
| 90 |  | 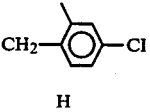 | H | I | N | 119–25 |
| 91 | 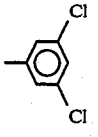 | H | H | H | CH | 105–07 |
| 92 | 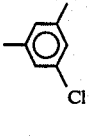 | H | H | H | N | 138 |
| 93 | 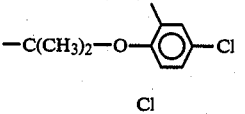 | H | H | H | CH | resin |
| 94 | 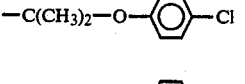 | H | H | H | N | resin |
| 95 | 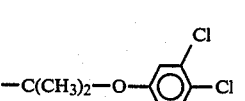 | H | H | H | CH | 96–98 |
| 96 | 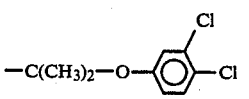 | H | H | H | CH | 106–07 |
| 97 | 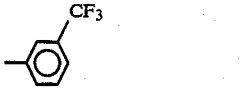 | H | H | H | N | 81–82 |
| 98 |  | H | H | H | CH | 124–27 |
| 99 |  | H | H | H | N | 103 |
USE EXAMPLES
The substances indicated below are employed as comparative compounds in the use examples which follow:

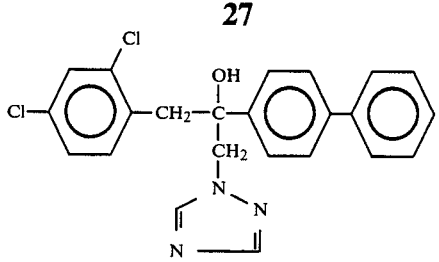

(A)

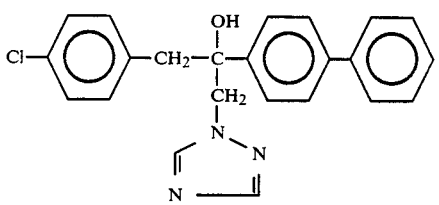

(B)

EXAMPLE A

Venturia test (apple)/protective

Solvent: 4.7 parts by weight of acetone
Emulsifier: 0.3 parts by weight of alkylaryl polyglycol ether To produce a suitable preparation of active compound, 1 parts by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organisms (Venturia inaequalis) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 29 and 16.

EXAMPLE B cl Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 29, 12, 10, 31, 14, 16, 20, 32, 72, 34, 35, 44, 45, 2, 46, 48 and 6.

EXAMPLE C

Pellicularia test (rice)

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

In this test, a clearly superior activity compared with the prior art is shown, for example, by the compounds according to the following preparation examples: 9, 10, 15, 14, 51, 29, 35, 31, 52, 12, 20, 16, 19, 44, 45, 47, 48, 70, 71 and 69.

It will be appreciated that the instant specification and examples are set forth by way of illustration and not limitation, and that various modifications and changes may be made without departing from the spirit and scope of the present invention.

What is claimed is:

1. A hydroxyalkinyl-azolyl derivative of the formula

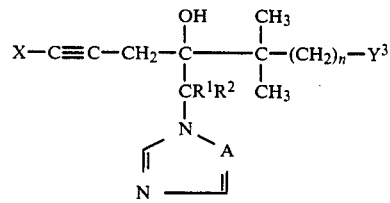

in which

A is a nitrogen atom or the CH group, $Y^3$ is phenoxy or phenylthio, phenylalkoxy having 1 to 4 carbon atoms in the alkyl part or phenylalkylthio having 1 to 4 carbon atoms in the alkyl part, the phenyl substituents in turn being optionally substituted by halogen and/or alkyl having 1 to 4 carbon atoms; alkoxy or alkylthio each having 1 to 2 carbon atoms; halogenoalkyl, halogenoalkoxy or halogenoalkylthio each having 1 to 2 carbon atoms and 1 to 5 identical or different halogen atoms; cyclohexyl, dialkylamino having 1 to 4 carbon atoms is each alkyl part, nitro, cyano, or alkoxycarbonyl having 1 to 4 carbon atoms in the alkyl part; phenyl or halophenyl;

n is 0, 1 or 2;

$R^1$ and $R^2$ each independently is hydrogen or methyl, and

X is hydrogen, bromine or iodine, or an addition product thereof with an acid or metal salt.

2. A compound according to claim 1, wherein such compound is 7-(4-chlorophenoxy)-5,5-dimethyl-4-(1,2,4-triazol-1-yl-methyl)-hept-1-in-4-ol of the formula

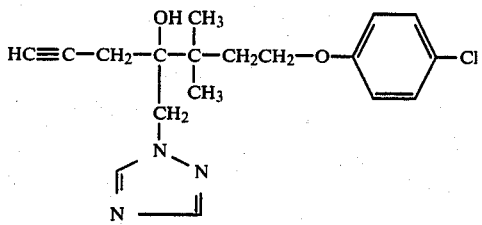

or an addition product thereof with an acid or metal salt.

3. A compound according to claim 1, wherein such compound is 6-(4-chlorophenoxy)-5,5-dimethyl-4-(1,2,4-triazol-1-yl-methyl)-hex-1-in-4-ol of the formula

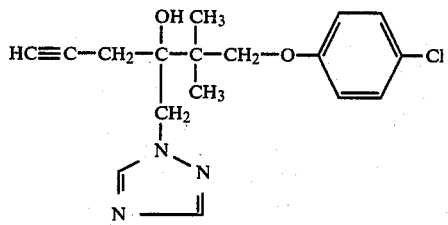

or an addition product thereof with an acid or metal salt.

4. A compound according to claim 1, wherein such compound is 7-phenoxy-5,5-dimethyl-4-(1,2,4-triazol-1-yl-methyl)-hept-1-in-4-ol of the formula

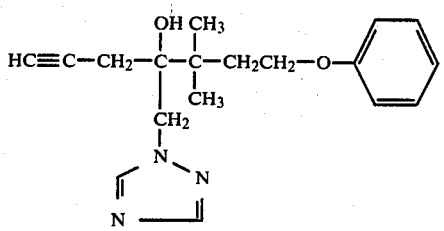

or an addition product thereof with an acid or metal salt.

5. A fungicidal composition comprising a carrier and a fungicidally effective amount of a compound or addition product according to claim 1.

6. A method of combating fungi which comprises administering to such fungi or to a habitat thereof a a fungicidally effective amount of a compound or addition product according to claim 1.

7. The method according to claim 6, wherein such compound is
7-(4-chlorophenoxy)-5,5-dimethyl-4-(1,2,4-triazol-1-yl-methyl)-hept-1-in-4-ol,
6-(4-chlorophenoxy)-5,5-dimethyl-4-(1,2,4-triazol-1-yl-methyl)-hex-1-in-4-ol, or
7-phenoxy-5,5-dimethyl-4-(1,2,4-triazol-1-yl-methyl)-hept-1-in-4-ol,
or an addition product thereof with an acid or metal salt.

* * * * *